US009046491B1

(12) United States Patent
Tripathi et al.

(10) Patent No.: US 9,046,491 B1
(45) Date of Patent: Jun. 2, 2015

(54) SURFACE AND RESONANCE-ENHANCED RAMAN DETECTION METHOD AND APPARATUS

(75) Inventors: Gorakh Nath Ram Tripathi, South Bend, IN (US); Pradeep R. Tripathi, Miami Beach, FL (US)

(73) Assignee: Nexus Enviromental, LLC, Miami Beach, FL (US)

( * ) Notice: Subject to any disclaimer, the term of this patent is extended or adjusted under 35 U.S.C. 154(b) by 339 days.

(21) Appl. No.: 13/488,550

(22) Filed: Jun. 5, 2012

Related U.S. Application Data

(60) Provisional application No. 61/493,740, filed on Jun. 6, 2011, provisional application No. 61/532,823, filed on Sep. 9, 2011.

(51) Int. Cl.
*G01N 21/00* (2006.01)
*G01N 21/65* (2006.01)
(52) U.S. Cl.
CPC .................................. *G01N 21/658* (2013.01)

(58) Field of Classification Search
None
See application file for complete search history.

(56) References Cited

U.S. PATENT DOCUMENTS 7,242,469 B2    7/2007  Wang et al.

OTHER PUBLICATIONS

Liang, H. et al. Normal and Surface-Enhanced Raman Spectroscopy of Nitroazobenzene Submonolayers and Multilayers on Carbon and Silver Surfaces, 2007, Applied Spectroscopy, vol. 61(6), pp. 613-620.*
Chowdhury, M. H. The Use of Surface Enhanced Raman Spectroscopy (SERS) for Biomedical Applications, 2005, Doctor of Philosophy Dissertation, Texas A&M University.*

* cited by examiner

*Primary Examiner* — Robert Xu
(74) *Attorney, Agent, or Firm* — Gardner, Linn, Burkhart & Flory, LLP

(57) ABSTRACT

A method and system for detecting a chemical using SERS includes shifting the absorption wavelength signature of the precursor chemical toward a higher wavelength. SERS is performed on the wavelength shifted chemical in order to determine the concentration of the precursor chemical.

4 Claims, 5 Drawing Sheets

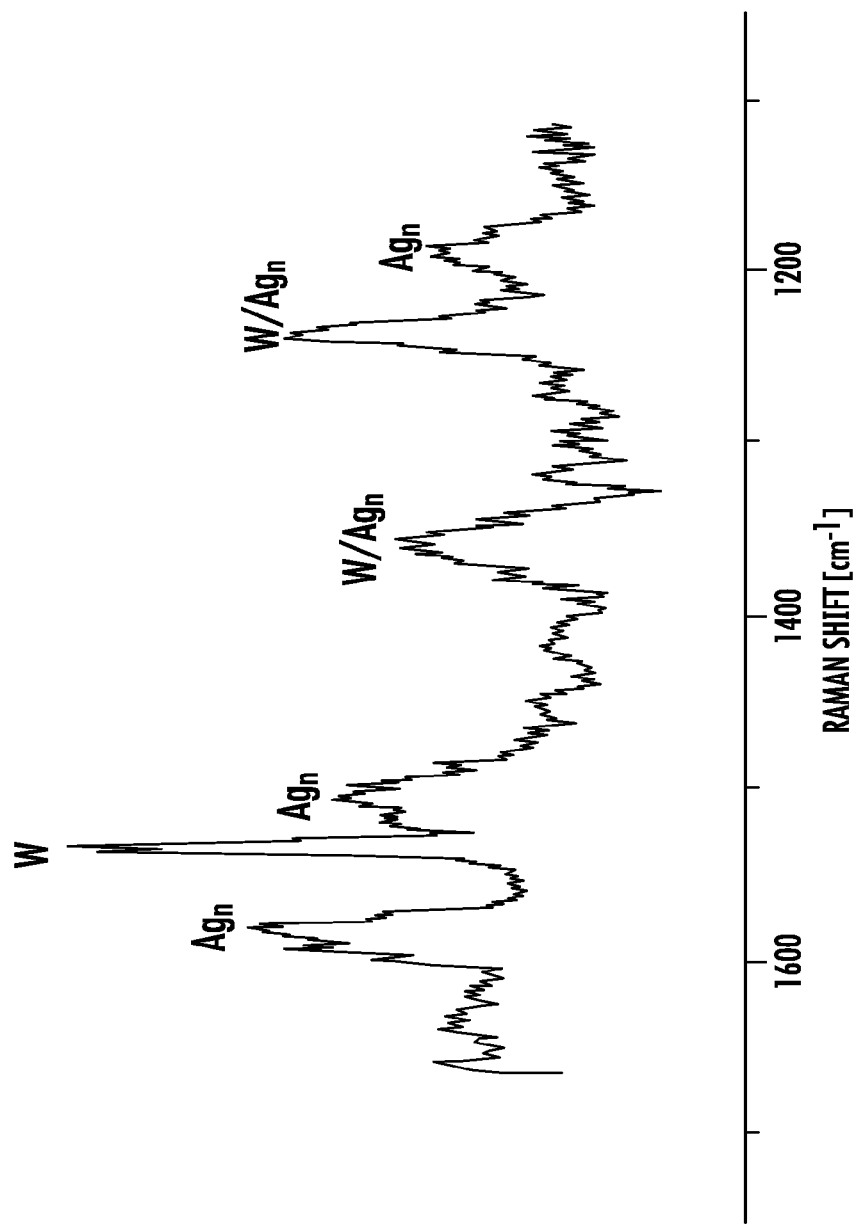
FIG. 5
RAMAN SPECTRUM OF A RADIATION-PRODUCED RADICAL ON SILVER NANO-PARTICLES IN WATER. THE PARENT MOLECULE IS NOT SEEN.
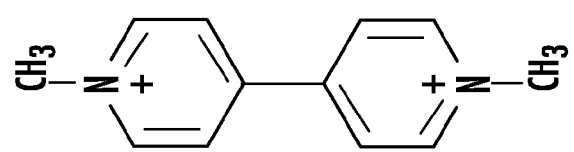

SURFACE AND RESONANCE-ENHANCED RAMAN DETECTION METHOD AND APPARATUS

CROSS-REFERENCE TO RELATED APPLICATIONS

This application claims priority from U.S. provisional patent application Ser. No. 61/493,740, filed on Jun. 6, 2011, and U.S. provisional patent application Ser. No. 61/532,823, filed on Sep. 9, 2011, the disclosures of which are hereby incorporated herein by reference in their entirety.

BACKGROUND OF THE INVENTION

The present invention is directed to a Raman detection method and apparatus and, in particular, to one incorporating molecular resonances in surface-enhanced Raman spectroscopy (SERS).

The essential components of a Raman detection system are 1) a source of monochromatic light (e.g., a laser providing a single wavelength/color), which impinges on a scattering object to be chemically analyzed, 2) a dispersive system (often a grating), which separates the different wavelengths present in the scattered light, and 3) a light detector, such as a PMT or CCD. The light detector records the intensity of the dispersed scattered light at different wavelengths. The shifts of the scattered wavelengths with respect to the monochromatic light incident on the scattering object and the intensity of the light at shifted wavelengths form the Raman spectrum (FIG. 1). A Raman spectrum contains fingerprint vibrational information on the scattering object, which is the primary advantage of using Raman scattering for chemical analysis. On the other hand, it is a very weak process, as seen in FIG. 2, and is not well suited to detecting chemical species in low concentration. Therefore, it initially found only limited industrial applications.

Because of fingerprint content of the Raman spectra, efforts have been made to improve the various components of the Raman detection system to enhance the spectral intensity. An example is a confocal Raman microscope, which is a commercial instrument that is widely used in scientific and industrial laboratories.

In addition to improving the efficiency of the conventional Raman system, as outlined above, the detection sensitivity can also be enhanced taking recourse to the physical principles involved in the scattering process. One of these processes is resonance Raman scattering, illustrated in FIG. 3, which can enhance the Raman signals, such as by a million times or more, when the Raman probe wavelength (monochromatic laser wavelength) coincides or nearly coincides with the absorption wavelength of the chemical. This high sensitivity comes at the cost of using different laser wavelengths for different chemicals. For that reason, it becomes a very expensive tool for chemical analysis and, therefore, impractical.

Another phenomenon related to the chemical species adsorbed on rough noble metal surfaces is termed as surface-enhanced Raman scattering (SERS). The Raman signals of a chemical species can be enhanced by several orders of magnitude by this process. A tremendous enhancement of the Raman scattering occurs when the chemical species is adsorbed on metal nanoparticles of about 30-150 nm dimensions. It is possible to detect chemical species at extremely low concentrations and, therefore, a potential wide applicability. One can use low expense visible lasers as monochromatic Raman probes in this case.

It is also known that a single molecule adsorbed on noble metal (e.g., silver, gold) nanoparticles can be detected in a few instances while retaining the fingerprint information. This detection method provides an even greater sensitivity with the fingerprint structural content specific to the chemical species adsorbed on the particle surface. However, this single molecule detection is limited to a very few molecules which tend to absorb in the visible spectrum. Therefore, the resonance Raman phenomenon may also be operative in addition to surface-enhanced Raman. Very few chemicals are the subjects of both phenomena occurring under similar physical and chemical conditions. Most chemicals absorb in ultraviolet and have no color.

SUMMARY OF THE INVENTION

The present invention provides enhanced detection sensitivity in a manner that broadens the scope of surface-enhanced Raman analytical applications. A method and system for detecting a chemical using SERS, according to an aspect of the invention, includes shifting the absorption wavelength signature of the precursor chemical toward a higher wavelength. SERS is performed on the wavelength shifted chemical in order to determine the concentration of the precursor chemical. The shifting of the absorption wavelength may include changing the redox state (FIGS. 3 and 4) and increasing the molecular size of the precursor chemical. The shifting of the absorption wavelength may be carried out using at least one transformation, such as i) chemical transformation, ii) photochemical transformation, and/or iii) radiation chemical transformation. The transformation may include inducing reduction or oxidation of the precursor chemical. The transformation may include applying ionizing radiation or far ultraviolet light to the precursor chemical.

The method and system may be used to detect an extremely low concentration of a chemical in the i) chemical industry, ii) biochemical industry, iii) food industry, iv) drug industry, v) environmental industry, vi) medical industry, vii) radiation safety industry, and/or viii) homeland security detection industry. The method and system may further include improving Raman detection sensitivity, such as by i) substrate manipulation, ii) light detector sensitivity, iii) spectrometer dispersion, and/or iv) probe light intensity.

These and other objects, advantages and features of this invention will become apparent upon review of the following specification in conjunction with the drawings.

BRIEF DESCRIPTION OF THE DRAWINGS

FIG. 5 is a diagram illustrating the detection of a viologen molecule (chemical structure on the left) in water by its reduction (shifting absorption to visible) and adsorption on silver nanoparticles. None of the Raman signals in the spectrum belong to the parent molecule.

DESCRIPTION OF THE PREFERRED EMBODIMENT

Figure 1:
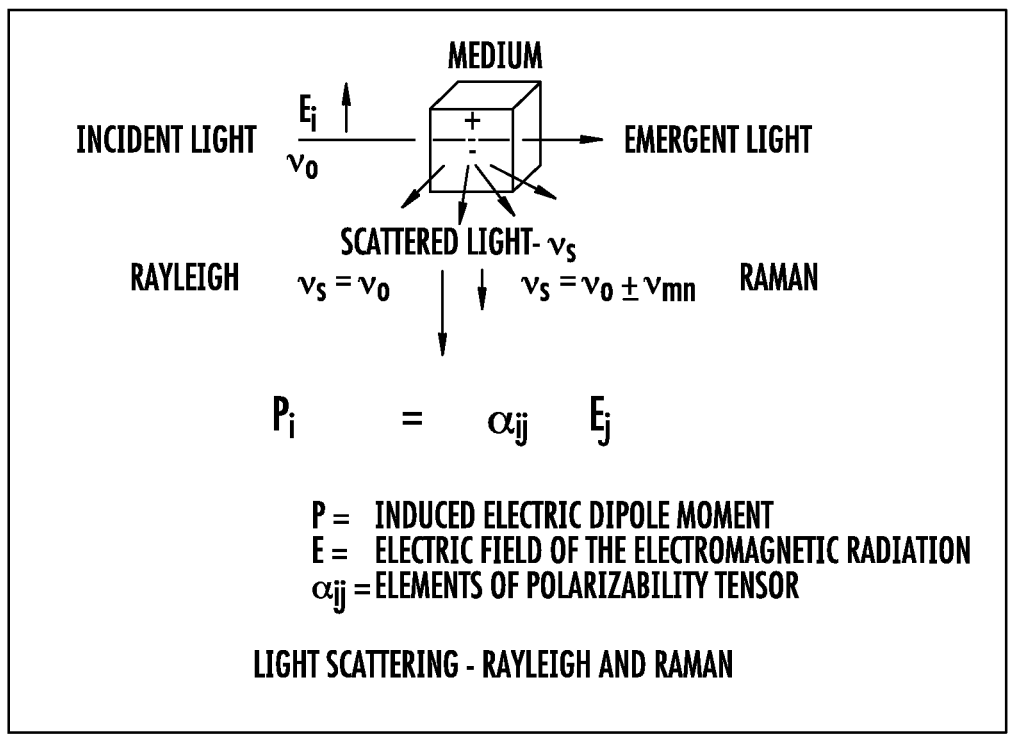
FIG. 1 is a diagram illustrating the scattering process and frequency shifts of the scattered wavelengths of a monochromatic light incident on the scattering object used for the Raman spectrum.
Figure 2:
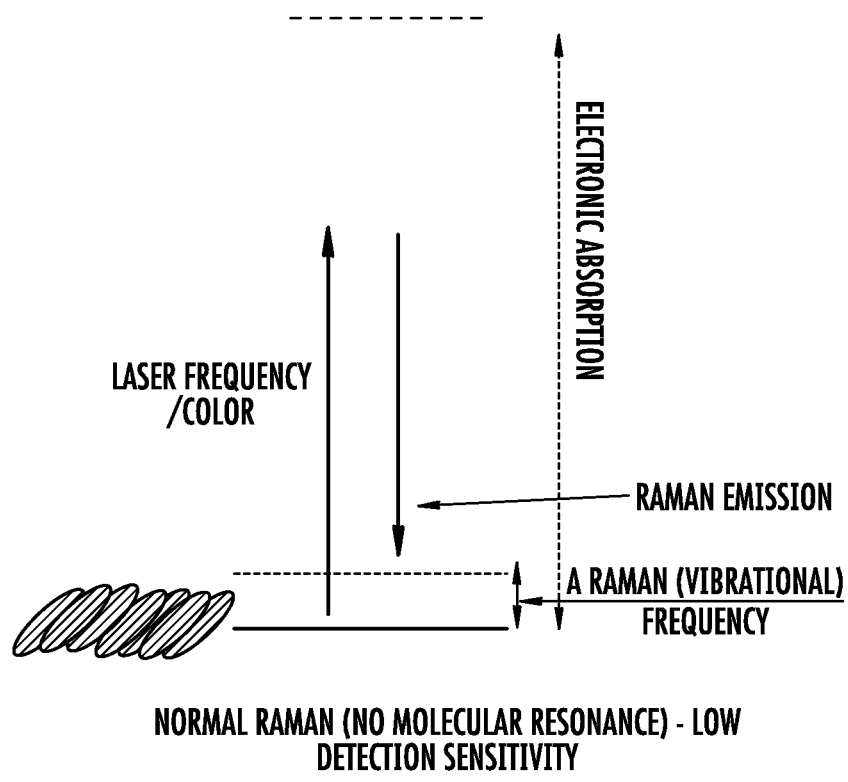
FIG. 2 is a diagram illustrating how the Raman spectrum contains fingerprint vibrational information on the scattering object.
Figure 3:
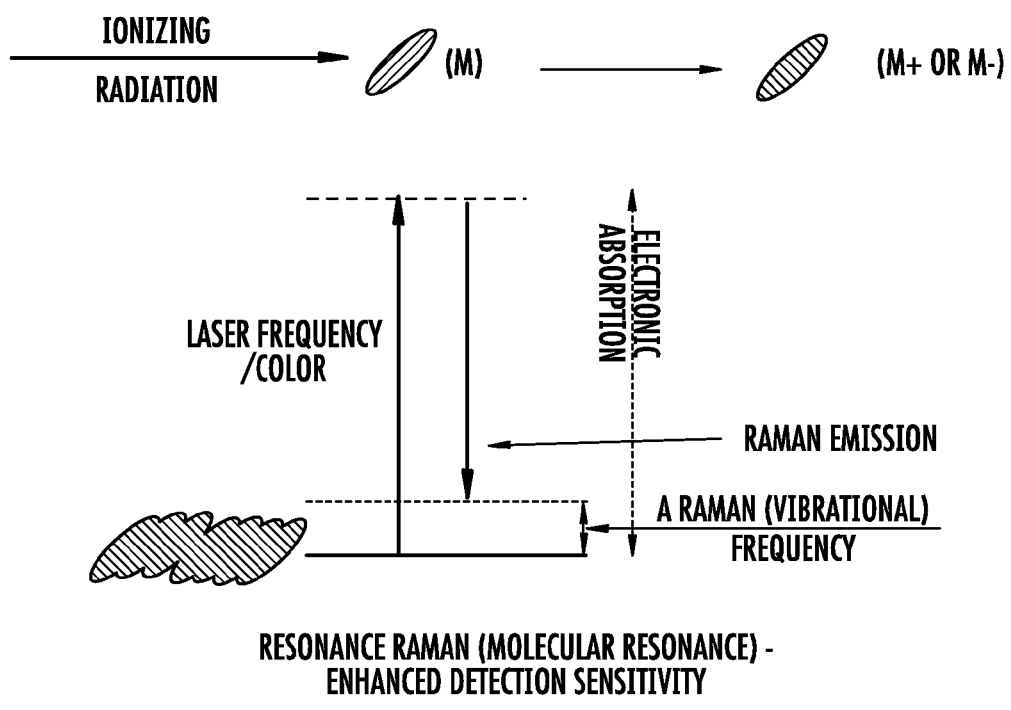
FIG. 3 is a diagram illustrating the use of resonance Raman scattering to enhance detection sensitivity. In a non-resonant system, the resonance enhancement can be induced by shifting the electronic absorption to a higher wavelength by oxidation or reduction of the molecule.
Figure 4:
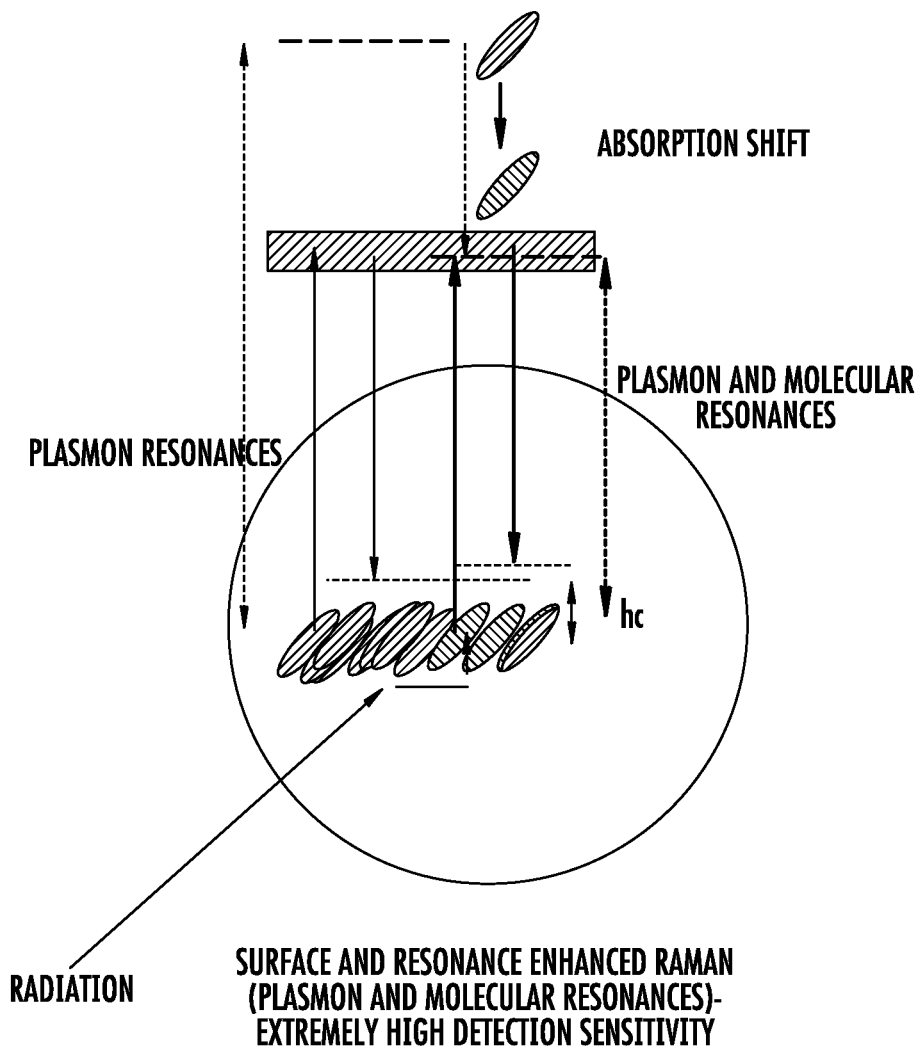
FIG. 4 is a diagram illustrating shifting of molecular absorption towards a higher wavelength where the metal particle also absorbs, thus combining surface enhancement with resonance enhancement of the Raman detection sensitivity.

The various embodiments of the invention can best be understood in the context of the current state of Raman analytical techniques. The detection sensitivity of chemical species can be increased tremendously if their absorption can be shifted towards a higher wavelength, as illustrated in FIGS. 4 and 5. Absorption can be shifted toward a higher wavelength by converting the molecules of the chemical into their radical state, and sometimes into larger dimer molecules and into polymers shifting the absorption towards the visible. This can be accomplished by chemical, photochemical or radiation chemical transformation of the chemicals. Most molecules in their redox intermediate state absorb in the visible or near visible region.

The detected irradiation products provide a measurement of their precursor molecules. The strength of ionizing radiation determines the number of molecules that are converted into their redox intermediate state absorbing in the visible (e.g., sulfur and nitrogen-containing aromatics) in a fixed time. The rate of conversion, however, can be independent of the radiation dose. Therefore, this approach provides a means of detecting ionizing radiation at an unprecedented low level. The embodiments disclosed herein may be even further enhanced by the conventional methods of improving Raman detection sensitivity, such as substrate manipulation, light detector sensitivity, spectrometer dispersion, probe light intensity, and the like.

Example 1

Thiophenols absorb in ultraviolet. However, thiophenols in water can be oxidized chemically, by UV oxidation (wavelength lower than 250 nm) or radiation chemical oxidation (OH radical is produced on the passage of gamma radiation or high energy electron/beta ray through water which can abstract an electron or hydrogen atom from the molecule) to produce compounds having more than two phenyl rings (bi-thiophenol) and absorbing at much higher wavelengths.

Example 2

Methyl viologen, which exhibits a moderate surface-enhanced Raman, can be detected with much higher sensitivity if converted to the corresponding radical by reduction that absorbs in the visible spectrum. This is illustrated in FIG. 5. These are two illustrative examples, but most molecules can be converted into visible or near visible absorbing radicals or their derivatives. Thus, it is seen that the present invention provides a unique approach for enhancing the detecting sensitivity of surface-enhanced Raman scattering (SERS) for chemical analysis. This enhanced sensitivity may be achieved by redox modification of chemicals that can be induced by ionizing radiation or UV light prior to their Raman detection and analysis. Such structural changes can also be incorporated by purely chemical methods; i.e., using an appropriate redox agent. This approach may be carried out in a simple manner and be applicable to a vast variety of chemical systems occurring in a host of situations; e.g., chemical, biochemical, food and drug industries and environmental, medical, radiation safety and homeland security related issues.

The enhanced detection sensitivity provided herein broadens the scope of surface-enhanced Raman analytical applications. Its applicability is not limited to only the industrial problems, but it can also be a valuable experimental tool in purely scientific investigations, such as the effect of background cosmic radiation on evolution of life forms, gene alteration and unexplained health issues associated with the environment. A common thread in all of these applications is the detection capability of a structure-sensitive tool for extremely low concentrations of chemicals, in some cases at a single molecule level, which this approach provides.

While the foregoing description describes several embodiments of the present invention, it will be understood by those skilled in the art that variations and modifications to these embodiments may be made without departing from the spirit and scope of the invention, as defined in the claims below. The present invention encompasses all combinations of various embodiments or aspects of the invention described herein. It is understood that any and all embodiments of the present invention may be taken in conjunction with any other embodiment to describe additional embodiments of the present invention. Furthermore, any elements of an embodiment may be combined with any and all other elements of any of the embodiments to describe additional embodiments.

The embodiments of the invention in which an exclusive property or privilege is claimed are defined as follows:

1. A method of detecting a chemical using SERS, said method comprising:
   shifting the absorption wavelength signature of the precursor chemical toward a higher wavelength and performing SERS on the wavelength shifted chemical in order to determine concentration of the precursor chemical wherein said shifting the absorption wavelength is carried out by radiation chemical transformation wherein said transformation comprises inducing reduction or oxidation of the precursor chemical by applying ionizing radiation or ultraviolet light to the precursor chemical.

2. The method as claimed in claim 1 used to detect a chemical in at least one industry chosen from the i) chemical industry, ii) biochemical industry, iii) food industry, iv) drug industry, v) environmental industry, vi) medical industry, vii) radiation safety industry, and viii) homeland security detection industry.

3. The method as claimed in claim 1 including further improving Raman detection sensitivity.

4. The method as claimed in claim 3 wherein said further improving Raman detection sensitivity comprises at least one chosen from i) substrate manipulation, ii) light detector sensitivity, iii) spectrometer dispersion, and iv) probe light intensity.

* * * * *